United States Patent
Du et al.

(10) Patent No.: US 12,188,022 B2
(45) Date of Patent: Jan. 7, 2025

(54) APTAMER FOR SPECIFICALLY RECOGNIZING SOLUBLE ST2 PROTEIN AND APPLICATION OF THE SAME

(71) Applicant: BEIJING INSTITUTE OF HEART, LUNG AND BLOOD VESSEL DISEASES, Beijing (CN)

(72) Inventors: Jie Du, Beijing (CN); Yuan Wang, Beijing (CN); Fengjuan Li, Beijing (CN); Xin Tan, Beijing (CN); Xue Wang, Beijing (CN)

(73) Assignee: BEIJING INST OF HEART LUNG & BLOOD VESSEL DISEASES, Beijing (CN)

( * ) Notice: Subject to any disclaimer, the term of this patent is extended or adjusted under 35 U.S.C. 154(b) by 0 days.

(21) Appl. No.: 18/435,472

(22) Filed: Feb. 7, 2024

(65) Prior Publication Data
US 2024/0229045 A1    Jul. 11, 2024

Related U.S. Application Data

(63) Continuation of application No. PCT/CN2022/119001, filed on Sep. 15, 2022.

(30) Foreign Application Priority Data

Mar. 18, 2022  (CN) .......................... 202210267054.9

(51) Int. Cl.
*C12N 15/115*    (2010.01)
*A61K 31/7088*   (2006.01)
*G01N 33/68*     (2006.01)

(52) U.S. Cl.
CPC ........ *C12N 15/115* (2013.01); *A61K 31/7088* (2013.01); *G01N 33/6893* (2013.01);
(Continued)

(58) Field of Classification Search
CPC .............. C12N 15/115; C12N 2310/16; C12N 2320/30; A61K 31/7088; A61K 49/0056;
(Continued)

(56) References Cited

FOREIGN PATENT DOCUMENTS

CN          112457392 A      3/2021

OTHER PUBLICATIONS

Lahkin (et al. 2013. Aptamers: Problems, Solutions and Prospects. Acta Naturae 5[4]:34-43) (Year: 2013).*
(Continued)

*Primary Examiner* — Kimberly Chong
*Assistant Examiner* — Ruth Sophia Arieti
(74) *Attorney, Agent, or Firm* — HAUPTMAN HAM, LLP

(57) ABSTRACT

A nucleic acid aptamer specifically recognizing soluble ST2 protein and its application, belonging to the field of variation or genetic engineering, are described. The technical problem addressed includes how to specifically detect sST2 protein. In order to address this technical problem, nucleic acid aptamers of single-stranded DNA with nucleotide sequences are shown in SEQ ID No. 1-10, respectively. SELEX technology, combined with high-throughput sequencing technology and bioinformatics analysis, reduces the rounds of screening and obtains candidate nucleic acid aptamers, and further analyzes its affinity and specificity to obtain a nucleic acid aptamer that specifically recognizes sST2 protein. The nucleic acid aptamer has the characteristics of high specificity, high stability, convenient synthesis, and easy labeling of functional groups, and the like, and may be used for the detection of sST2 protein and the preparation of biosensors, diagnosis and prognosis of cardiovascular diseases and other products.

5 Claims, 2 Drawing Sheets

Specification includes a Sequence Listing.

(52) U.S. Cl.
CPC ...... *C12N 2310/16* (2013.01); *C12N 2320/30* (2013.01); *G01N 2800/321* (2013.01); *G01N 2800/323* (2013.01); *G01N 2800/324* (2013.01); *G01N 2800/325* (2013.01); *G01N 2800/52* (2013.01)

(58) Field of Classification Search
CPC ........... A61K 49/0067; G01N 33/6893; G01N 2800/321; G01N 2800/323; G01N 2800/324; G01N 2800/325; G01N 2800/52; G01N 33/6869; G01N 2333/7155; G01N 2800/329; A61P 9/04; A61P 9/10; A61P 9/14
See application file for complete search history.

(56) References Cited

OTHER PUBLICATIONS

Zhou (and Rossi. 2016. Aptamers as targeted therapeutics: current potential and challenges. Nat. Rev. Drug Discov. 16:181-202) (Year: 2016).*
Homsak (and Gruson. 2020. Soluble ST2: A complex and diverse role in several diseases. Clinica Chimica Acta 507:75-87) (Year: 2020).*
Filali (et al. 2021. Soluble ST2, a biomarker of fibrosis, is associated with multiple risk factors, chronic diseases and total mortality in the OPERA study. Scandinavian J. Clinical Lab. Investig. 81[4]:324-331) (Year: 2021).*
Jiang (et al. 2022. An IL1RL1 genetic variant lowers soluble ST2 levels and the risk effects of APOE-ε4 in female patients with Alzheimer's disease. Nat. Aging 616[2]:616-634) (Year: 2022).*
Forga (et al. 2021. Relationship between soluble protein ST2 (sST2) levels and microvascular complications in a cohort of patients with type 1 diabetes. Endocrinología, Diabetes y Nutrición 69:322-330) (Year: 2022).*
Alzheimers.gov (2024. Can I prevent dementia? Available online at alzheimers.gov. Accessed on Jun. 4, 2024) (Year: 2024).*
Mayo Clinic (2024. Type 1 diabetes. Available online at mayoclinic.org. Accessed on Jun. 4, 2024) (Year: 2024).*
First Office Action issued in Chinese Application No. 202210267054.9; mailed Apr. 22, 2022; 18 pgs.
Wang, Qing, et al; "Screening of DNA Aptamers against Myoglobin Using Positive and Negative Selection Units Integrated Microfluidic Chip and its Biosensing Application"; Analytical Chemistry, vol. 86, No. 13; Jun. 10, 2014, 27 pgs.
International Search Report issued in International Application No. PCT/CN2022/119001; mailed Dec. 15, 2022.

* cited by examiner

SEQUENCE LISTING

```
Sequence total quantity: 13
SEQ ID NO: 1              moltype = DNA   length = 35
FEATURE                   Location/Qualifiers
source                    1..35
                          mol_type = other DNA
                          organism = synthetic construct
SEQUENCE: 1
tccatccact cggggctaga agccgtgaga atctg                              35

SEQ ID NO: 2              moltype = DNA   length = 35
FEATURE                   Location/Qualifiers
source                    1..35
                          mol_type = other DNA
                          organism = synthetic construct
SEQUENCE: 2
tccatccact cgggccctag ggcgtgtatg tccat                              35

SEQ ID NO: 3              moltype = DNA   length = 35
FEATURE                   Location/Qualifiers
source                    1..35
                          mol_type = other DNA
                          organism = synthetic construct
SEQUENCE: 3
tccatccact cggcctacta agggtttcgt tcacc                              35

SEQ ID NO: 4              moltype = DNA   length = 36
FEATURE                   Location/Qualifiers
source                    1..36
                          mol_type = other DNA
                          organism = synthetic construct
SEQUENCE: 4
tccatccact cggggcgggg gctcgtgctc tatttc                             36

SEQ ID NO: 5              moltype = DNA   length = 35
FEATURE                   Location/Qualifiers
source                    1..35
                          mol_type = other DNA
                          organism = synthetic construct
SEQUENCE: 5
cctccatcca ctcggcgcaa cgccggggct cggcc                              35

SEQ ID NO: 6              moltype = DNA   length = 35
FEATURE                   Location/Qualifiers
source                    1..35
                          mol_type = other DNA
                          organism = synthetic construct
SEQUENCE: 6
tccattcact cgaccgctga cgcgggtgtc gtttt                              35

SEQ ID NO: 7              moltype = DNA   length = 35
FEATURE                   Location/Qualifiers
source                    1..35
                          mol_type = other DNA
                          organism = synthetic construct
SEQUENCE: 7
tccatgcact cgcccttgaa agggttccct ccgtt                              35

SEQ ID NO: 8              moltype = DNA   length = 35
FEATURE                   Location/Qualifiers
source                    1..35
                          mol_type = other DNA
                          organism = synthetic construct
SEQUENCE: 8
tccatccact cggcgccacg cggtttctcc agatt                              35

SEQ ID NO: 9              moltype = DNA   length = 35
FEATURE                   Location/Qualifiers
source                    1..35
                          mol_type = other DNA
                          organism = synthetic construct
SEQUENCE: 9
tccatgcact cgcgctaccg gcgtgcccgt agatc                              35

SEQ ID NO: 10             moltype = DNA   length = 35
FEATURE                   Location/Qualifiers
source                    1..35
                          mol_type = other DNA
                          organism = synthetic construct
```

```
SEQUENCE: 10
tccattcact cgcagcgggg tcgcgtgagg cgcaa                              35

SEQ ID NO: 11            moltype = DNA  length = 75
FEATURE                  Location/Qualifiers
source                   1..75
                         mol_type = other DNA
                         organism = synthetic construct
SEQUENCE: 11
gacaggcagg acaccgtaac nnnnnnnnnn nnnnnnnnnn nnnnnnnnnn nnnnnctgct   60
acctccctcc tcttc                                                    75

SEQ ID NO: 12            moltype = DNA  length = 20
FEATURE                  Location/Qualifiers
source                   1..20
                         mol_type = other DNA
                         organism = synthetic construct
SEQUENCE: 12
gacaggcagg acaccgtaac                                               20

SEQ ID NO: 13            moltype = DNA  length = 20
FEATURE                  Location/Qualifiers
source                   1..20
                         mol_type = other DNA
                         organism = synthetic construct
SEQUENCE: 13
gaagaggagg gaggtagcag                                               20
```

APTAMER FOR SPECIFICALLY RECOGNIZING SOLUBLE ST2 PROTEIN AND APPLICATION OF THE SAME

RELATED APPLICATIONS

The present application is a Continuation of International Application Number PCT/CN2022/119001 filed Sep. 15, 2022, which claims priority to Chinese Application Number 202210267054.9 filed Mar. 18, 2022, the disclosures of which are hereby incorporated by reference herein in their entireties.

INCORPORATION BY REFERENCE

The sequence listing provided in the file entitled sequencePUS1230454_0204.xml, which is an Extensible Markup Language (XML) file that was created on Feb. 3, 2024, and which comprises 12,824 bytes, is hereby incorporated by reference in its entirety.

TECHNICAL FIELD

The present invention relates to an aptamer which can specifically recognize soluble ST2 protein and the use thereof in the field of genetic engineering.

BACKGROUND OF THE INVENTION

Aptamer, which is screened by an in vitro technology—a systematic evolution of ligands by exponential enrichment (SELEX) technology, is defined as screening a single-stranded DNA (ssDNA) or RNA that specifically binds to a target molecule from a random deoxy oligonucleotide library. The traditional antigen-antibody reaction has a good sensitivity and specificity. Enzyme-linked immunosorbent assay plays a pivotal role in the detection of various biomolecules. However, as a probe molecule, a protein is easily denatured by environmental factors such as pH and temperature, and this approach is expensive due to the high cost of such synthesis. The essence of aptamer is a single-stranded DNA or RNA molecule that folds to form a specific three-dimensional structure and binds to biological targets with high affinity and high specificity. Due to it has a small molecular weight, the following incomparable advantages can be achieved by using aptamer technology: synthesized using chemical approach, modified and labelled structurally allowable, has a stable structure, reversibly denatured and refolded allowable, can be stored and transported at room temperature, and has low immunogenicity and toxicity compared to tranditional immunology and chemical molecular recognition method. In the field of biomedical technology, aptamers can be used in many aspects such as clinical diagnosis, drug delivery, and drugs for treatment of disease. For example, aptamers have the following characteristics required as a targeting agent: can be binded to radionuclides, can be delivered to the target tissue, can directly inhibit target protein.

The aptamer-based technologies has therapeutic application potential in vivo imaging and therapeutic drug. Currently, the aptamer-based technologies have been widely used in the following aspects: identifying as drug targets, using as drug molecules or lead molecules, and using as biological missiles to guide targeted therapy. In addition, aptamers can bind to a variety of target substances with high specificity and selectivity, and often cause conformational changes when bind to target molecules, by using aptamers the binding force between labeled aptamers and target molecules will not change. These characteristics make the biochemical detection technology of aptamers receive great attention. Currently, aptamers have been widely used in various sensors, such as electrochemical sensors, optical sensors and acoustic sensors etc.

Growth stimulation expressed gene2 (ST2) is a member of interleukin 1 receptor/Toll-like receptor superfamily. ST2 protein has two forms, a soluble form (sST2) and a membrane-bound receptor form (ST2L), and the functional ligand of ST2 is interleukin-33 (IL-33). Studies in recent years have shown that ST2 is closely related to cardiovascular diseases in addition to participating in inflammatory reactions. The soluble ST2 (sST2) is a decoy receptor for IL-33, which blocks IL-33 from binding to ST2L by competitively binding to IL-33, and then weakens the cardiovascular protection of IL-33/ST2 signaling pathway. A series of experimental and clinical studies have found that the increase of sST2 level is related to the severity of heart failure and can predict the occurrence of sudden cardiac death. It is a good marker for evaluating the risk stratification of heart failure. sST2 is currently one of the most specific indicators for heart failure detection. It is hardly affected by age, gender, BMI, etiology of heart failure, atrial fibrillation, anemia, and renal function. It has low biological variability and high stability, and may be applied in diagnosis of heart failure, predicting the prognosis of heart failure, refining the clinical stratification of heart failure, predicting the probability of death of patients and other clinical applications. In addition, recent studies have also found that sST2 can identify and diagnose patients with aortic aneurysm/dissection, and may be used as a diagnostic marker for acute aortic dissection. However, the current clinical detection of sST2 is based on the detection of antigen and antibody, and the detection kit thereof is expensive, which limits its therapeutic application. Therefore, a more accurate, stable, convenient and affordable sST2 detection scheme is still needed. The aptamers can specifically bind to the target and is expected to be used in the clinical detection of sST2 and disease treatment.

SUMMARY OF THE INVENTION

The object of the present invention is to provide a group of aptamers that specifically recognize sST2 proteins and/or the application of the same in sST2 protein detection, and the aptamers have high specificity, high stability, convenient synthesis and/or are easily labelled with functional groups. The technical problems to be solved are not limited to the described technical subjects, and those skilled in the art can clearly understand other technical subjects not mentioned herein through the following description.

In order to achieve the above object, the present invention firstly provides aptamers that specifically recognizes sST2 protein, and the aptamers may be any one of the following:

A1) any single-stranded DNA with a nucleotide sequence shown in any one of SEQ ID No. 4, 6, 5, 1, 2, 3, 7, 8, 9 or 10;

A2) any single-stranded DNA with a nucleotide sequence having 75% or more identity with the nucleotide sequence defined in A1), and specifically recognizing sST2 protein;

A3) any single-stranded RNA that is transcribed from the single-stranded DNA shown in A1) and specifically recognizes sST2 protein;

A4) any single-stranded RNA or single-stranded RNA that hybridizes with the nucleotide sequence defined in A1) or A3) under stringent conditions, and specifically recognizes sST2 protein.

sST2 protein is a soluble growth stimulation expressed gene 2 protein.

The identity of 75% or more may be an identity of 80%, 85%, 90% or more.

Herein, the identity of more than 80% may be an identity of at least 80%, 81%, 82%, 83%, 84%, 85%, 86%, 87%, 88%, 89%, 90%, 91%, 92%, 93%, 94%, 95%, 96%, 97%, 98%, or 99%.

Further, the aptamers may be linked with functional groups or molecules.

Further, the 5' end or 3' end of the aptamers is modified with functional groups or molecules.

Further, the functional groups or molecules may be isotopes, fluorescent labels, chemiluminescent labels, bioluminescent labels, enzyme labels, magnetic substances, biotin, affinity ligands, mercapto groups and/or therapeutic substances.

The functional group or molecule is used to improve the stability of the aptamers, provide a detection signal, or bind the aptamers to other substances so as to form a composition.

The present invention also provides a probe, which may be a substance obtained by labeling any aptamer with a label.

The label means any atom or molecule which may be used to provide a detectable (preferably quantifiable) effect and which may be attached to a nucleic acid. Labels include, but are not limited to, dyes; radiolabels, such as $^{32}P$; conjugated coupling groups, such as biotin; haptens, such as digoxigenin (DIG); chemiluminescent, phosphorescent, or fluorescent moieties; and fluorescent dyes alone or fluorescent dyes combined with moieties that can suppress or shift the emission spectrum through fluorescence resonance energy transfer (FRET). Labels can provide signals detected by fluorescence, radioactivity, colorimetric, gravimetric, quantum dot, electrochemical, X-ray diffraction or absorption, magnetic, immunoenzyme labeling reaction, filter paper-based immunoassay, affinity precipitation, affinity chromatography, enzyme activity, microscopic projection or scanning imaging, super-resolution imaging, cell tracking, living nanoparticle tracking and tracking imaging of animals or humans, nano-flow cytometry, adjustable resistance pulse induction, fluorescence correlation spectroscopy surface plasmon resonance, fluorescence polarization, surface-enhanced Raman spectroscopy, electrochemical sensing, microfluidics or microfluidics, chip analysis, proteomics, genomics, metabolomics, microbiomics, RNA (mRNA, lnRNA, snRNA), miRNA, and the like. Labels may be charged moieties (positive or negative charge) or optionally, may be charge neutral. Labels may comprise a nucleic acid or protein sequence, or a combination thereof, so long as the sequence comprising the label is detectable. In some embodiments, the nucleic acid is directly detected (e.g., the sequence is read directly) without a label. The labels can also be used for targeted drug delivery.

In some embodiments, the labels are fluorophores, colorimetric labels, quantum dots, biotin, and other label molecules that may be used for detection (such as alkyne groups for Raman diffraction imaging, cycloolefins for click reactions, initiating groups for polymer labeling), can also be selected from polypeptide/protein molecules, LNA/PNA, non-natural amino acids and their analogs (such as peptidomimetics), non-natural nucleic acids and their analogs (pseudo-nucleotides) and nanostructures (including inorganic nanoparticles, NV-center, aggregation/assembly-induced luminescent molecules, rare earth ion ligand molecules, polymetallic oxygen clusters, and the like).

In some embodiments, the fluorophore may be selected from fluorescein-based dyes, rhodamine-based dyes, and cyanine dyes.

In some embodiments, the fluorescein dyes include standard fluorescein and its derivatives, such as fluorescein isothiocyanate (FITC), hydroxyl fluorescein (FAM), tetrachlorofluorescein (TET), cy5, cy3, Quasar 670, Alexa Fluor 488/647, and the like.

In some embodiments, the rhodamine-based dyes include R101, tetraethylrhodamine (RB200), carboxytetramethylrhodamine (TAMRA), and the like.

In some embodiments, the cyanine dyes are mainly selected from two types, one is thiazole orange (TO), oxazole orange (YO) series and their dimer dyes, and the other is cyanine dyes of polymethylene series.

In some embodiments, the fluorophore can also be selected from the following dyes: stilbenes, naphthalimides, coumarins, acridines, pyrenes, and the like.

The fluorophore is usually labeled at the 5' end of the probe sequence, but it can also be placed at the 3' end by changing the modification bond (such as —OH or —NH bond).

In one embodiment of the present invention, the 5' end of the single-stranded DNA (ssDNA) aptamer described in SEQ ID No. 1-10 is labeled with Biotin.

The present invention also provides a sensor, which contains any one of the aptamers or any one of the probes.

The present invention also provides a reagent or a kit for detecting sST2 protein, the reagent or kit contains any one of the aptamers or any one of the probes described herein.

The kit also includes one or more of Taq DNA polymerase, dNTP, PCR buffer and $Mg^{2+}$ required for PCR amplification.

The various reagent components of the kit may be present in separate containers, or may be pre-combined in whole or in part into a reagent mixture.

The present invention also provides a drug for preventing, improving or treating sST2 related diseases, the drug containing any one of the aptamers or any one of the probes described herein.

Further, the drug also contains one or more pharmaceutically acceptable carriers.

The pharmaceutically acceptable carrier may be a diluent, excipient, filler, binder, wetting agent, disintegrant, absorption accelerator, adsorption carrier, surfactant or lubricant.

The present invention also provides a drug delivery system specifically targeting sST2 protein, the drug delivery system containing any one of the aptamers or any one of the probes described herein.

The drug delivery system may be a liposome drug delivery system, a polymer micelle drug delivery system, a polymer disk drug delivery system or a nanoparticle drug delivery system.

The drug delivery system is used for targeted delivery and/or fixed-point release of drugs.

The present invention also provides any one of the following applications of any one of the aptamers or any one of the probes described herein:

B1) Application in the preparation of a drug or product for the prevention, improvement or treatment of sST2 related diseases;

B2) Application in detection of sST2 protein or preparation of a product for detection of sST2 protein;

B3) Application in the preparation of a product for binding to sST2 protein;

B4) Application in the preparation of a product for in vivo imaging of sST2 protein;

B5) Application in the preparation of a product for screening, diagnosis or auxiliary diagnosis of sST2 related diseases;

B6) Application in the preparation of a product for prognostic assessment of sST2 related diseases;

B7) Application in the preparation of a product for predicting the probability of death of patients with sST2 related diseases;

B8) Application in the preparation of a product for assessing heart failure risk stratification.

In the above application, the sST2 related diseases may be cardiovascular diseases.

In the above application, the cardiovascular disease includes heart failure, atherosclerosis, hypertension, myocardial infarction, coronary heart disease, acute coronary syndrome, aortic aneurysm or aortic dissection, but is not limited thereto.

The present invention also provides a method for detecting sST2 protein, the method comprising labeling a reporter group on any one of aptamers shown in SEQ ID No. 1-10, making the aptamers labeled with the reporter group interact with the sample to be detected, and realizing the detection of sST2 protein through the signal detection of the reporter group.

Further, the reporter group may be biotin or a fluorescent group, and the fluorescent group may be Rhodamine, FAM (Carboxyfluorescein), FITC(Fluorescein isothiocyanate), BODIPY(Boron-dipyrromethenes), Cy3(Cyanine3), Cy5 (Cyanine5), VIC(2'-chloro-7'phenyl-1,4-dichloro-6-carboxy-fluorescein), HEX(Hexadecimal), TET(Tetrachlorofluorescein), ROX(Carboxy-X-rhodamine), JOE(5'-Dichloro-dimethoxy-fluorescein), TAMRA (Tetramethylrhodamine), but is not limited thereto.

The objects of the above-mentioned applications and methods may be disease diagnosis, disease prognosis and/or disease treatment objects, and their objects may also be non-disease diagnosis objects, non-disease prognosis objects and non-disease treatment objects; their direct objects may be to obtain intermediate results on of disease diagnostic results, disease prognosis results, and/or disease treatment results, and their direct objects may be non-disease diagnosis objects, non-disease prognosis objects, and/or non-disease treatment objects.

The aptamers described herein may be single-stranded DNA (ssDNA) aptamers or single-stranded RNA (ssRNA) aptamers.

The sST2 related diseases described herein may be diseases caused by abnormal IL-33/ST2 signaling pathway.

The products described herein may be kits, test strips or biosensors.

The present invention also provides any one of the following applications of any one of the aptamers or probes described herein:

C1) Application in the prevention, improvement or treatment of sST2 related diseases;

C2) Application in in vivo imaging of sST2 protein;

C3) Application in screening, diagnosis or auxiliary diagnosis of sST2 related diseases;

C4) Application in prognostic assessment of sST2 related diseases;

C5) Application in predicting the probability of death of patients with sST2 related diseases;

C6) Application in assessing heart failure risk stratification;

C7) Application in treatment monitoring of sST2 related diseases;

C8) Application in purification of sST2 protein.

In the above application, sST2 related diseases may be cardiovascular diseases.

In the above application, the cardiovascular disease may include heart failure, atherosclerosis, hypertension, myocardial infarction, coronary heart disease, acute coronary syndrome, aortic aneurysm or aortic dissection, but is not limited thereto.

The present invention also provides a method for screening, diagnosing or assisting in diagnosing sST2 related diseases, the method may include: obtaining a sample containing serum, blood or plasma from a subject, and then detecting the content of sST2 protein in the sample using the aptamers described herein, and screening, diagnosis or auxiliary diagnosis of sST2 related diseases according to the content of sST2 protein.

The present invention also provides a method for treating sST2 related diseases, the method comprising administering the aptamers or sST2 inhibitor coupled to the aptamers to a subject who has been diagnosed with an sST2 related disease.

In the above method, the sST2 inhibitor may be an agent that inhibits the ST2L/IL-33 signaling pathway.

In the above method, the sST2 related disease may be cardiovascular disease.

In the above method, the cardiovascular disease may include heart failure, atherosclerosis, hypertension, myocardial infarction, coronary heart disease, acute coronary syndrome, aortic aneurysm or aortic dissection, but is not limited thereto.

The invention adopts MCP-SELEX technology, combines high-throughput sequencing technology and bioinformatics analysis, reduces the rounds of screening and obtains candidate aptamers. Its affinity and specificity is further analyzed, so as to obtain ssDNA aptamers specifically recognizing sST2 protein. The ssDNA aptamer of the present invention has the characteristics of high specificity, high stability, convenient synthesis, easy labeling of functional groups, and the like, can specifically recognize and bind to sST2 protein, and is used for the detection of sST2 protein and the preparation of biosensors. At the same time, ssDNA aptamers of the present invention are also potential therapeutic drugs for sST2 related diseases, and may be used to prepare reagents for clinical diagnosis or drugs for disease treatment.

The invention provides high-specificity aptamers that may be screened in vitro, may be obtained in high throughput, has a short screening period, is convenient to synthesize, has good stability, high affinity, and is easy to modify and label for the detection of sST2. At the same time, the aptamers of the present invention may be used alone or combined with related drugs, and has development prospects for the treatment of diseases in which sST2 is involved.

BEST MODE OF IMPLEMENTING THE PRESENT INVENTION

The present invention will be further described in detail below in conjunction with specific embodiments, and the given examples are only for clarifying the present invention, not for limiting the scope of the present invention. The examples provided below may be used as a guideline for those skilled in the art to make further improvements, and are not intended to limit the present invention in any way.

Figure 1:
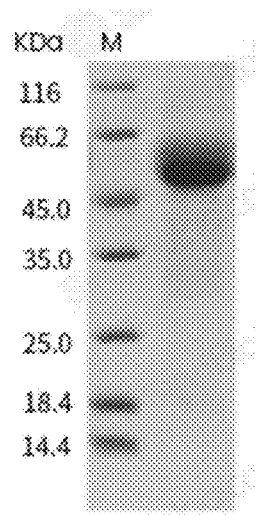
FIG. 1 is a diagram of the purified electrophoresis results of human sST2 protein.

The experimental methods in the following examples, unless otherwise specified, are conventional methods, carried out according to the techniques or conditions described in the literature in this field or according to the product instructions. The materials and reagents used in the following examples may be obtained from commercial sources unless otherwise specified.

sST2 protein in the following examples was purchased from Beijing Sino Biological Technology Co., Ltd. (Cat: 10105-H08H). The results of its purification electrophoresis (SDS-PAGE) are shown in FIG. 1.

Example 1. Screening of Single-Stranded DNA Aptamers Targeting Human SST2 Protein Single-stranded DNA (ssDNA) aptamers targeting human sST2 protein was obtained by using systematic evolution of ligands by exponential enrichment (SELEX) and high-throughput sequencing technology, and by applying bioinformatics analysis.

Specific steps are as follows:
1. Construction of a Random SsDNA Library

The random ssDNA library comprises two primer regions and a random region of 35 bases, the nucleotide sequence of which is shown in SEQ ID No.11, wherein positions 1-20 of SEQ ID No.11 are the forward primer region, positions 56-75 of SEQ ID No.11 are a reverse primer region, positions 21-55 of SEQ ID No.11 are 35 nucleotides N, and N represents A, G, C or T.

Wherein the forward primer sequence corresponding to the forward primer region is:

(SEQ ID No. 12)
5'-GACAGGCAGGACACCGTAAC-3';

The reverse primer sequence corresponding to the reverse primer region is:

(SEQ ID NO. 13)
5'-GAAGAGGAGGGAGGTAGCAG-3'.

2. Magnetic Bead Negative Screening
   2-1. Dissolve 10 μl of 100 mM random ssDNA library in 480 ml of Binding buffer (137 mM NaCl; 2.7 mM KCl; 4.3 mM $Na_2HPO_4$; 1.4 mM $KH_2PO_4$), heat in a water bath at 95° C. for 10 min, and quench in an ice bath for 10 min, and left at room temperature for 10 min to prepare a library of ssDNA aptamers that form secondary structures.

2-2. Activation of the magnetic beads. The magnetic beads are treated with 50 mg/mL EDC and 50 mg/mL NHS to form carboxylated magnetic beads. Wash twice with 25 mM MES solution (pH=5.0) and add 10 μL Binding Buffer, disperse the magnetic beads in Binding Buffer, ready for use.

2-3. Add all the activated magnetic beads to the ssDNA library solution with a total volume of 500 μL, incubate at room temperature for 30 min, discard the magnetic beads after the incubation (magnetic separation), and keep the supernatant.

3. Magnetic Bead Screening for SsDNA Bound to the Target Molecule (SST2)
   3-1. Add 10 μL of 10 μM sST2 protein to the supernatant, and rotate at 25° C. for 1 h.
   3-2. Activation of the magnetic beads, the steps are the same as those in 2-2 above.
   3-3. Add the activated magnetic beads to the ssDNA solution for incubating sST2, and incubate at room temperature for 30 min. After the incubation, discard the supernatant and keep the magnetic beads.
   3-4. After adding 500 μL of Binding Buffer to the magnetic beads, place them on a shaker for 5 minutes, place them on a strong magnet for 1 minute, take out the supernatant, repeat washing 4 times (5 minutes each time), and collect each supernatant (W1-W4).
   3-5. Add 1.8 μL Proteinase K (20 mg/mL) to the washed magnetic beads, dilute to 120 μL with Binding Buffer, place in a 52° C. incubator for 2 h, shake at 95° C. after the reaction and heat for 20 min to inactivate Proteinase K, and take out 120 μL of supernatant, which is the eluate of the first round of screening (R1).

4. Preparation of the SsDNA Library for the Next Round of Screening
   4-1. Use the eluent (R1) as a template to prepare a small PCR sample, set different numbers of amplification rounds, and judge which cycle has the least amplification concentration and impure amplification bands by gel electrophoresis. The number of amplification rounds is usually set as 5, 9, 12, 15, 18, 21, and a blank control should be added when PCR is carried out. The system for the small sample PCR is shown in Table 1.

TABLE 1

| System for small sample PCR (20 ul) | |
| --- | --- |
| Components | Volume |
| Taq enzyme | 10 ul |
| Water | 4 ul |
| Forward primer | 2 ul (a primer with Biotin is used) |
| Reverse primer | 2 ul (a primer with Biotin is used) |
| Template | 2 ul |
| Total volume | 20 ul |

Taking samples that have completed predetermined rounds of amplification at 72° C. extension.

4-2. Large Sample PCR

After small sample PCR, judge the optimal number of amplification rounds by gel electrophoresis experiment, and perform a large sample PCR according to the number of amplification rounds. 6-8 tubes are needed with a volume of 100 μl for each tube. The system for the large sample PCR is shown in Table 2.

TABLE 2

System for large sample PCR (100 ul)

| Components | Volume |
|---|---|
| Taq enzyme | 50 ul |
| Water | 20 ul |
| Forward primer | 10 ul (a primer with Biotin is used) |
| Reverse primer | 10 ul (a primer with Biotin is used) |
| Template | 10 ul |
| Total volume | 100 ul |

4-3. Preparation of Single Stranded DNA (Secondary Library)

① Slowly pass the products obtained after large sample PCR through the streptomycin coated agarose beads one by one. After all the samples pass through the column, wash them twice with 200 μl PBS.

② Add 100 μl of NaOH, the collected liquid after passing through the column is the target single stranded DNA, add 2 μl of 15 M HCL (hydrochloric acid) to neutralize, and mix well.

③ Detect the concentration of the collected single stranded DNA (ssDNA) solution as the library for the next round of screening.

5. Fluorescent Quantitative PCR Detection and Screening the Enrichment Degree of Library 5-1. Using the supernatant W1-W4 collected in step 3-4 and the eluate R1 of the first round as templates, perform fluorescent quantitative PCR.

5-2. The elution ratio, binding ratio and signal-to-noise ratio of each round of screening may be obtained through the number of cycles of fluorescent quantitative PCR and the standard curve, and the enrichment degree of the library may be evaluated based on these references.

6. Multiple Rounds of Screening and High Throughput Sequencing 6-1. Repeat the screening steps 1-5, and use the secondary library obtained in the previous round as the initial library for each screening. During the screening process, the screening pressure was increased by reducing the amount of library input and adding negative screening proteins to increase the enrichment degree of the ssDNA library.

Figure 2:
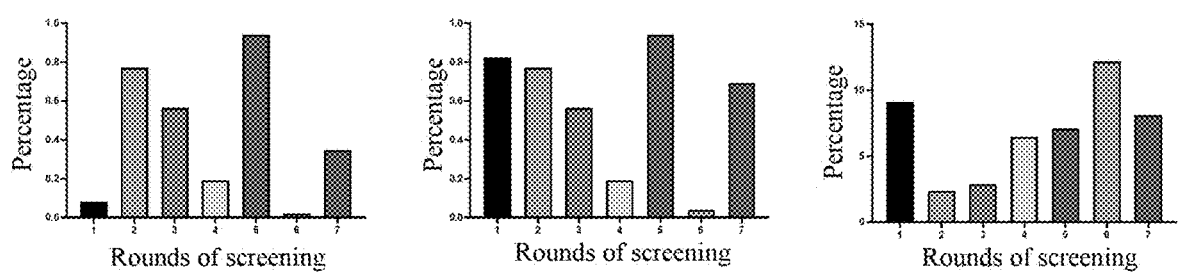
FIG. 2 shows the percentage of elution ratio (first from left), binding ratio (second from left), and signal-to-noise ratio (third from left) after the $1^{st}$, $2^{nd}$, $3^{rd}$, $4^{th}$, $5^{th}$, $6^{th}$, and $7^{th}$ round of screening.

6-2. After 7 rounds of screening, the results of fluorescent quantitative PCR show that the ssDNA library has been significantly enriched, much higher than the $6^{th}$ round (results shown in FIG. 2), so the ssDNA from the $6^{th}$ and $7^{th}$ rounds were amplified by PCR. The amplified and purified products were subjected to high throughput sequencing. By comparing the abundance of the sequencing results, the top 10 DNA sequences were determined, and their nucleotide sequences are shown in Table 3.

TABLE 3

Sequence information of the top 10 aptamers in terms of abundance

| Name | SEQ ID No. | Length | Sequence (5'-3') |
|---|---|---|---|
| Apt1 | SEQ ID No. 1 | 35 | TCCATCCACTCGGGGCTAGAAGCCGTGAGAATCTG |
| Apt2 | SEQ ID No. 2 | 35 | TCCATCCACTCGGGCCCTAGGGCGTGTATGTCCAT |
| Apt3 | SEQ ID No. 3 | 35 | TCCATCCACTCGGCCTACTAAGGGTTTCGTTCACC |
| Apt4 | SEQ ID No. 4 | 36 | TCCATCCACTCGGGGCGGGGCTCGTGCTCTATTTC |
| Apt5 | SEQ ID No. 5 | 35 | CCTCCATCCACTCGGCGCAACGCCGGGGCTCGGCC |
| Apt6 | SEQ ID No. 6 | 35 | TCCATTCACTCGACCGCTGACGCGGGTGTCGTTTT |
| Apt7 | SEQ ID No. 7 | 35 | TCCATGCACTCGCCCTTGAAAGGGTTCCCTCCGTT |
| Apt8 | SEQ ID No. 8 | 35 | TCCATCCACTCGGCGCCACGCGGTTTCTCCAGATT |
| Apt9 | SEQ ID No. 9 | 35 | TCCATGCACTCGCGCTACCGGCGTGCCCGTAGATC |
| Apt10 | SEQ ID No. 10 | 35 | TCCATTCACTCGCAGCGGGGTCGCGTGAGGCGCAA |

Example 2. Gel Electrophoretic Mobility Assay (EMSA) to Detect the Binding of Aptamers to SST2 Protein EMSA (Electrophoretic Mobility Shift Assay) is an in vitro technique for detecting the interaction between protein and DNA sequence (or RNA sequence), which may be used for qualitative and quantitative analysis. Purified proteins and DNA sequences (or RNA sequences) are usually incubated in a homogeneous environment, followed by separation of protein-DNA complexes and non-binding sequences on non-denaturing polyacrylamine (PAGE) gel electrophoresis. The principle of separation is that the protein-DNA complex moves slower than the non-binding sequence due to the binding of macromolecular substances such as proteins on the DNA.

The experimental steps are as follows:

1. DNA Heat Treatment

According to the experimental formula shown in Table 4, the aptamer was added to the buffer solution and nuclease-free water, heated at 95° C. for 10 minutes, quenched on ice for 10 minutes, and room temperature for 10 minutes.

TABLE 4

DNA heat treatment experimental formula

| Number of Sample | Aptamer (20 μM) | sST2 (10 μM) | Buffer solution (2 × binding buffer) | Nuclease-free water | Total volume |
|---|---|---|---|---|---|
| Negative Control | 2 μL | — | 10 μL | 8 μL | 20 μL |
| Experimental Group | 2 μL | 8 μL | 10 μL | — | 20 μL |

2. Incubation of DNA and Target

The above DNA solution and sST2 protein were slowly mixed to a final volume of 20 μL, and a sample containing only aptamer and no protein was used as a negative control, and incubated with rotation at room temperature for 30 minutes.

3. Gel Electrophoresis

Figure 3:
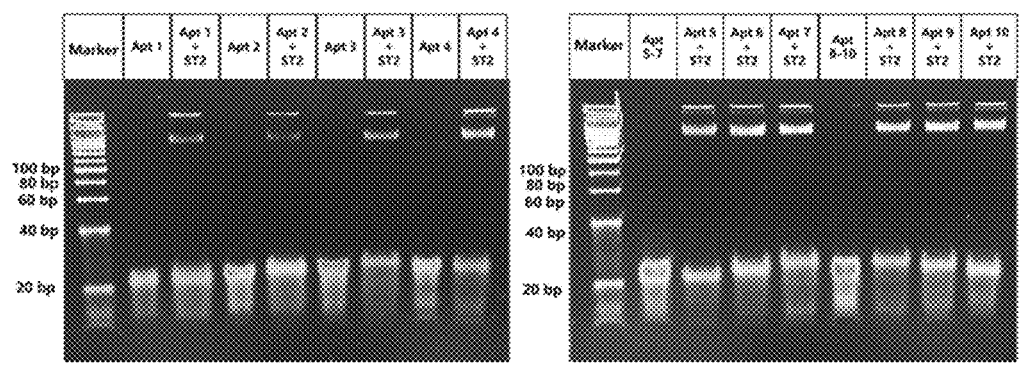
FIG. 3 shows the EMSA (Electrophoretic Mobility Shift Assay) experimental result in Example 2.

Non-denaturing PAGE gel electrophoresis was performed on negative controls and samples, gel imaging was performed after dye staining, and analysis was performed with imaging software. The results are shown in FIG. 3, all of the aptamers Apt1-10 shown in SEQ ID No.1-10 strongly bind to sST2, wherein the binding of Apt4 shown in SEQ ID No.4, Apt5 shown in SEQ ID No.5 and Apt6 shown in SEQ ID No.6 is more significant.

Example 3. Determination of Affinity of Apt4, Apt5 and Apt6 to SST2 Protein

1. Incubate the detection target sST2 protein with the silanized and bifunctionalized optical fiber at room temperature for 6 h.
2. The DNA of Apt4, Apt5 and Apt6 was labeled with CY5.5, and the DNA of Apt4, Apt5 and Apt6 were prepared in different concentrations: 0 nM, 10 nM, 50 nM, 100 nM, 200 nM, 500 nM, and 1000 nM.
3. Load the optical fiber into the detection instrument, and each concentration of aptamer passes through the detection instrument in turn according to the steps set in the sample injection (as shown in Table 5).

TABLE 5

Injection setting steps

| Injection steps | Injection time | Waiting time |
|---|---|---|
| Buffer solution | 20 s | 5 s |
| Sample (A48-cy5) | 20 s | 180 s (binding) |
| Buffer solution | 20 s | 180 s (dissociation) |
| Regeneration solution | 30 s | 5 s |
| Buffer solution | 30 s | 0 s |

The composition of buffer solution in Table 5 is 137 mM NaCl; 2.7 mM KCl; 4.3 mM $Na_2HPO_4$; 1.4 mM $KH_2PO_4$; the regeneration solution is 2 M NaCl.

Figure 4:
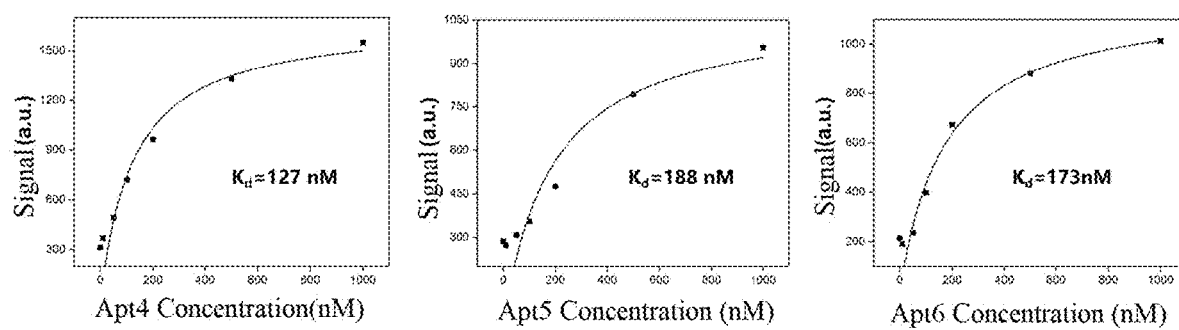
FIG. 4 shows the results of affinity detection experiments between aptamers Apt4 (SEQ ID No.4), Apt5 (SEQ ID No.5) and Apt6 (SEQ ID No.6) and sST2 protein in Example 3.

4. Record the fluorescence photometry value of each concentration gradient DNA entering the detector, and use the GraphPad Prism software to perform curve fitting based on the measured fluorescence photometry value, and use the equation $Y=Bmax*X/(Kd+X)$ to calculate the Kd value. The results are shown in FIG. 4, the binding value Kd of Apt4 shown in SEQ ID No.4 to sST2 protein is 127 nM, the binding value Kd of Apt5 shown in SEQ ID No.5 to sST2 protein is 188 nM, and the binding value Kd of Apt6 shown in SEQ ID No. 6 to sST2 protein is 173 nM.

The present invention has been described in detail above. For those skilled in the art, without departing from the spirit and scope of the present invention, and without unnecessary experiments, the present invention may be practiced in a wider range under equivalent parameters, concentrations and conditions. While specific examples of the invention have been given, it should be understood that the invention may be further modified. In one word, according to the principles of the present invention, this application intends to include any changes, uses or improvements to the present invention, including changes made with conventional techniques known in the art and departing from the disclosed scope of this application. Applications of some of the essential features are possible within the scope of the appended claims below.

INDUSTRIAL APPLICATION

The invention adopts MCP-SELEX technology, combines high throughput sequencing technology and bioinformatics analysis, reduces the rounds of screening and obtains candidate aptamers. Further analysis of its affinity and specificity resulted in the ssDNA aptamer specifically recognizing sST2 protein. The ssDNA aptamer of the present invention has the characteristics of high specificity, high stability, convenient synthesis, easy labeling of functional groups, and the like, can specifically recognize and bind to sST2 protein, and is used for the detection of sST2 protein and the preparation of biosensors. At the same time, ssDNA aptamer of the present invention is also a potential therapeutic drug for sST2 related diseases, and may be used to prepare reagents for clinical diagnosis or drugs for disease treatment.

The present invention provides highly specific aptamers that may be screened in vitro, may be obtained in high throughput, has a short screening period, is convenient to synthesize, has good stability, high affinity, and is easy to modify and label for the detection of sST2. The aptamers may be chemically synthesized, does not rely on biology, is cheap, and is easy to store. At the same time, the aptamers of the present invention may be used alone or carry related drugs, and has development prospects for the treatment of diseases in which sST2 is involved.

What is claimed:

1. A nucleic acid aptamer, comprising any one of the following:
   (A1) a single-stranded DNA with the nucleotide sequence shown in SEQ ID No 4;
   (A2) a single-stranded DNA with the nucleotide sequence shown in SEQ ID No. 6;
   (A3) a single-stranded DNA with the nucleotide sequence shown in SEQ ID No. 5;
   (A4) a single-stranded DNA with the nucleotide sequence shown in SEQ ID No. 1;
   (A5) a single-stranded DNA with the nucleotide sequence shown in SEQ ID No. 2;
   (A6) a single-stranded DNA with the nucleotide sequence shown in SEQ ID No. 3;
   (A7) a single-stranded DNA with the nucleotide sequence shown in SEQ ID No. 7;
   (A8) a single-stranded DNA with the nucleotide sequence shown in SEQ ID No. 8;
   (A9) a single-stranded DNA with the nucleotide sequence shown in SEQ ID No. 9; or
   (A10) a single-stranded DNA with the nucleotide sequence shown in SEQ ID No. 10.

2. A probe comprising any one of the nucleic acid aptamers according to claim 1 and a reporter group linked to the nucleic acid aptamer.

3. A sensor containing any one of the nucleic acid aptamers according to claim 1.

4. A reagent or kit for detecting sST2 protein, wherein the reagent or kit contains any one of the nucleic acid aptamers according to claim 1.

5. A method for detecting sST2 protein, wherein the method comprises:
   (1) labelling the nucleic acid aptamer of claim 1 with a reporter group;
   (2) supplying the reporter group-labelled nucleic acid aptamer to a sample to be tested so that the reporter group-labelled nucleic acid aptamer binds to sST2 protein in the sample; and
   (3) detecting sST2 protein by detecting the signal of the reporter group.

* * * * *